(12) United States Patent
Augustine et al.

(10) Patent No.: US 6,254,557 B1
(45) Date of Patent: *Jul. 3, 2001

(54) WOUND TREATMENT APPARATUS WITH INFRARED ABSORPTIVE WOUND COVER

(75) Inventors: Scott D. Augustine, Bloomington; John P. Rock, Minneapolis; Albert P. Van Duren, Chaska, all of MN (US)

(73) Assignee: Augustine Medical, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/655,380

(22) Filed: Sep. 5, 2000

Related U.S. Application Data (63) Continuation of application No. 09/055,725, filed on Apr. 6, 1998.

(51) Int. Cl.⁷ ............................................. A61F 7/00
(52) U.S. Cl. .................. 602/2; 602/14; 602/42; 607/96; 607/114
(58) Field of Search .......................... 602/2, 14, 41–55; 607/96, 108–110, 114

(56) References Cited

U.S. PATENT DOCUMENTS

| | | | |
|---|---|---|---|
| 5,662,624 | * | 9/1997 | Sundstrom et al. ............. 602/2 |
| 5,817,145 | * | 10/1998 | Augustine et al. .............. 602/2 |
| 5,986,163 | * | 11/1999 | Augustine ....................... 602/2 |
| 6,134,475 | | 10/2000 | Will . |

FOREIGN PATENT DOCUMENTS

94/00090 * 1/1994 (WO) ................................. 602/2

* cited by examiner

Primary Examiner—Robert L. Nasser
(74) Attorney, Agent, or Firm—Gray Cary Ware Freidenrich (57) ABSTRACT

A wound treatment apparatus is provided which includes a bandage that absorbs energy in the infrared (IR) range of the electromagnetic spectrum, a heater that generates heat, and an attachment apparatus for retaining the heater over or on the bandage. The bandage and heater together have a low profile so as to be convenient for a patient and are flexible so as to conform to the shape of a wound and to contours of the skin near the wound. The bandage is provided with an adhesive pattern for maintaining moisture at the wound site. The heater may maintain a normothermic condition at the wound treatment area. A controller may be provided for cycling the temperature of the heater in order to maintain the normothermic condition.

22 Claims, 7 Drawing Sheets

WOUND TREATMENT APPARATUS WITH INFRARED ABSORPTIVE WOUND COVER

CROSS-REFERENCES TO RELATED PATENT AND COPENDING APPLICATIONS

This application is a continuation of U.S. patent application Ser. No. 09/055,725, filed Apr. 6, 1998.

This application contains material related to U.S. patent application Ser. No. 08/843,072 filed on Apr. 11, 1997 entitled "FLEXIBLE NON-CONTACT WOUND TREATMENT DEVICE WITH A SINGLE JOINT" and to the following commonly assigned pending U.S. Patent Applications:

Ser. No. 07/900,656, filed Jun. 19, 1992, for "THERMAL BODY TREATMENT APPARATUS AND METHOD";

Ser. No. 08/342,741, filed Nov. 21, 1994, for WOUND TREATMENT DEVICE";

Ser. No. 08/356,325, filed Feb. 21, 1995, for "WOUND COVERING";

Ser. No. 08/785,794, filed Jan. 21,1997, for "NORMOTHERMIC HEATER WOUND COVERING";

Ser. No. 08/786,713, filed Jan. 21, 1997, for "NORMOTHERMIC TISSUE HEATING WOUND COVERING";

Ser. No. 08/786,714, filed Jan. 21, 1997, for "NEAR HYPOTHERMIC HEATER WOUND COVERING"; and Ser. No. 08/838,618, filed Apr. 11, 1997, for "FLEXIBLE NON-CONTACT WOUND TREATMENT DEVICE".

This application also contains material related to the following commonly assigned U.S. Patent Applications, which were concurrently filed with this application:

Ser. No. 09/056,191, filed Apr. 6, 1998 for "WOUND TREATMENT APPARATUS WITH A HEATER, A HEAT CONDUCTIVE BANDAGE, AND A HEAT-SPREADING MEANS ACTING BETWEEN THE HEATER AND BANDAGE";

Ser. No. 09/056,063, filed Apr. 6, 1998 for "WOUND TREATMENT APPARATUS INCLUDING A HEATER AND AN IR-TRANSPARENT OR IR-TRANSMISSIVE BANDAGE";

Ser. No. 09/055,597, filed Apr. 6, 1998 for "WOUND TREATMENT APPARATUS WITH IR TRANSPARENT OR IR TRANSMISSIVE WOUND COVER"; and Ser. No. 09/055,605, filed Apr. 6, 1998 for "WOUND TREATMENT APPARATUS FOR NORMOTHERMIC TREATMENT OF WOUNDS".

STATEMENT OF REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

The present invention relates to a wound treatment apparatus with a bandage that is essentially absorptive in the infrared range of the electromagnetic spectrum and a heater that emits energy in the IR range. The bandage and heater are connected or joined by an attachment means that holds the heater in position on or over the bandage.

2. Description of the Related Art

Wounds, in general, are breaks in the integrity of the skin of a patient. A first type of wound may result from mechanical trauma that produces a cut, tear, or an abrasion. There are many instruments of causality for such wounds, including knives, glass, gravel, or a scalpel. A second type of wound may be caused by a combination of heat and pressure wherein the heat alone is insufficient to cause an outright burn. Such wounds include pressure sores, decubitus ulcers, or bed sores, and reflect an injury that is chronic in nature. A wound may also be vascular in origin. In this third type of wound, blood flow through a region may be altered sufficiently to cause secondary weakening of tissues which are eventually disrupted, thus forming a wound. In the case of arterial causes, the primary difficulty is getting oxygenated blood to the affected area. For venous causes, the primary difficulty is fluid congestion in the affected area which backs up, decreasing the flow of oxygenated blood. Because these wounds manifest underlying chronic disease processes. such as atherosclerotic vascular disease, congestive heart failure, and diabetes, these vascular injuries also are chronic in nature, forming wounds with ulcerated bases.

Heat therapy has been used to treat wounds since the days of Hippocrates, with varying results. Up to now, heat therapy for wounds has involved the application of heat under conditions that make the tissues of a wound hyperthermic. Hyperthermia impedes wound healing and may actually damage the wound tissues.

The "normal" range of temperature for the human body is $37°$ C.$\pm 1°$ C. ($36°$ C.–$38°$ C.). This range is referred to as "normothermic". Humans exhibit a thermoregulatory response to core temperature changes as little as $\pm 0.1°$ C., wherein "icore" as used herein refers to interior portions of the body. This extremely tight temperature control is necessary because virtually all cellular functions, chemical reactions and enzymatic reactions are optimum at normothermia.

Surface tissue varies in temperature according to where on the body it is located. The skin of the torso is usually hypothermic, while the skin of the legs is always hypothermic. The normal skin temperature of the distal leg is approximately $32°$ C., which is considered to be "moderately hypothermic". The skin temperature of the distal leg of a patient with vascular insufficiency may be as low as $25°$ C., which is "severely hypothermic". The hypothermic condition of wounds and ulcers inhibits healing. Severely hypothermic skin or wound tissue is in a state that may be termed "suspended animation". In suspended animation, tissue is living, but cellular functions necessary for cell division and collagen deposition are slowed or even stopped. Further, the immune system is inhibited, allowing wounds to become heavily colonized with bacteria. The local application of heat to hypothermic skin will cause some degree of vasodilatation, resulting in an increase in local blood flow. Increased blood flow increases the subcutaneous oxygen tension ($PsqO_2$) which, in turn, increases both collagen deposition and immune function.

Many references report that the immune system is inhibited by hypothermia and activated by mild hyperthermia (fever). Persp Biol Med:439–474, Spring 1980, reports that local body temperature is a critical factor determining host susceptibility, the location of lesions and contracting infectious diseases. New Eng J Med 305:808–814, 1981, reports that animals exposed to cold environments are more susceptible to infectious diseases, whereas exposure to high ambient temperatures often produces a beneficial result. Wound Rep Reg 2:48–56, 1994 and Acta Anaesth Scand 38:201–205, 1994, report that infections caused by a standard inoculum of *e. coli* or *s. aureus* were significantly more severe in hypothermic guinea pigs than in normothermic control animals. New Eng J Med 334:1209–1215, 1996, reports that hypothermic colorectal surgical patients had three times more wound infections (19% vs. 6%) than those who were kept normothermic during surgery with a Bair Hugger® patient warming system described in commonly assigned U.S. Pat. Nos. 5,324,320, 5,300,102 and 5,350,417. Further, six weeks of warming therapy with the Bair Hugger® patient warming system has successfully healed chronic progressive ulcers which heretofore have been resistant to standard therapies.

Currently available medical apparatuses that apply heat to wounds include infrared lights, warm water pads, warm water bottles, whirlpools and Sitz baths. All types of lesions, such as surgical, chronic, traumatic, donor sites, infected wounds and burns, have been treated with these warming modalities. Particularly difficult has been the application of heat to open wounds such as ulcers. Treatment of a wound with infrared light requires that the wound be positioned under the light during therapy, necessitating patient immobility. Further, the infrared heat causes wounds to dry, thereby slowing the healing process. Warm water pads and bottles and electrical heating pads are cumbersome, reduce patient mobility, and are usually applied to the extremities and held in place with inconvenient wraps such as straps, hook-and-eye material or tabs. Whirlpools and Sitz baths reduce mobility and limit the duration of warming therapy due to skin maceration by the water. None of these modalities is capable of prolonged heat treatment of a wound.

SUMMARY OF THE INVENTION

There is a need for a wound treatment apparatus to treat a wound with heat for a prolonged period of time, while promoting patient convenience and mobility. Preferably, the treatment would produce a substantially normothermic condition at the wound. It is also important that the wound treatment apparatus be flexible and have a low profile for convenience of the patient. Such a wound treatment apparatus should efficiently transfer heat to a treatment site, be convenient to operate without adversely impacting the patient, and be capable of maintaining a moist wound environment.

Preferably, the operation of the wound treatment apparatus is referred to a "wound treatment area" (or "treatment area") that may include the wound, unwounded skin adjacent the wound (the periwound), or both.

The invention is a wound treatment apparatus that includes three parts. First is a wound bandage that absorbs energy in the infrared (IR) range of the electro-magnetic spectrum. The second part is a heater that is disposed on or over the bandage. The heater emits a significant amount of its energy in the IR range. The third part of the invention is an attachment means to hold the heater in position over the bandage.

Other objects and advantages of the invention will become apparent upon reading the following description taken together with the accompanying drawings.

DESCRIPTION OF THE PREFERRED EMBODIMENTS

Referring now to the figures, wherein like reference numerals designate like or similar parts throughout the several views there are shown various embodiments of a wound treatment apparatus according to this invention.

Figure 1:
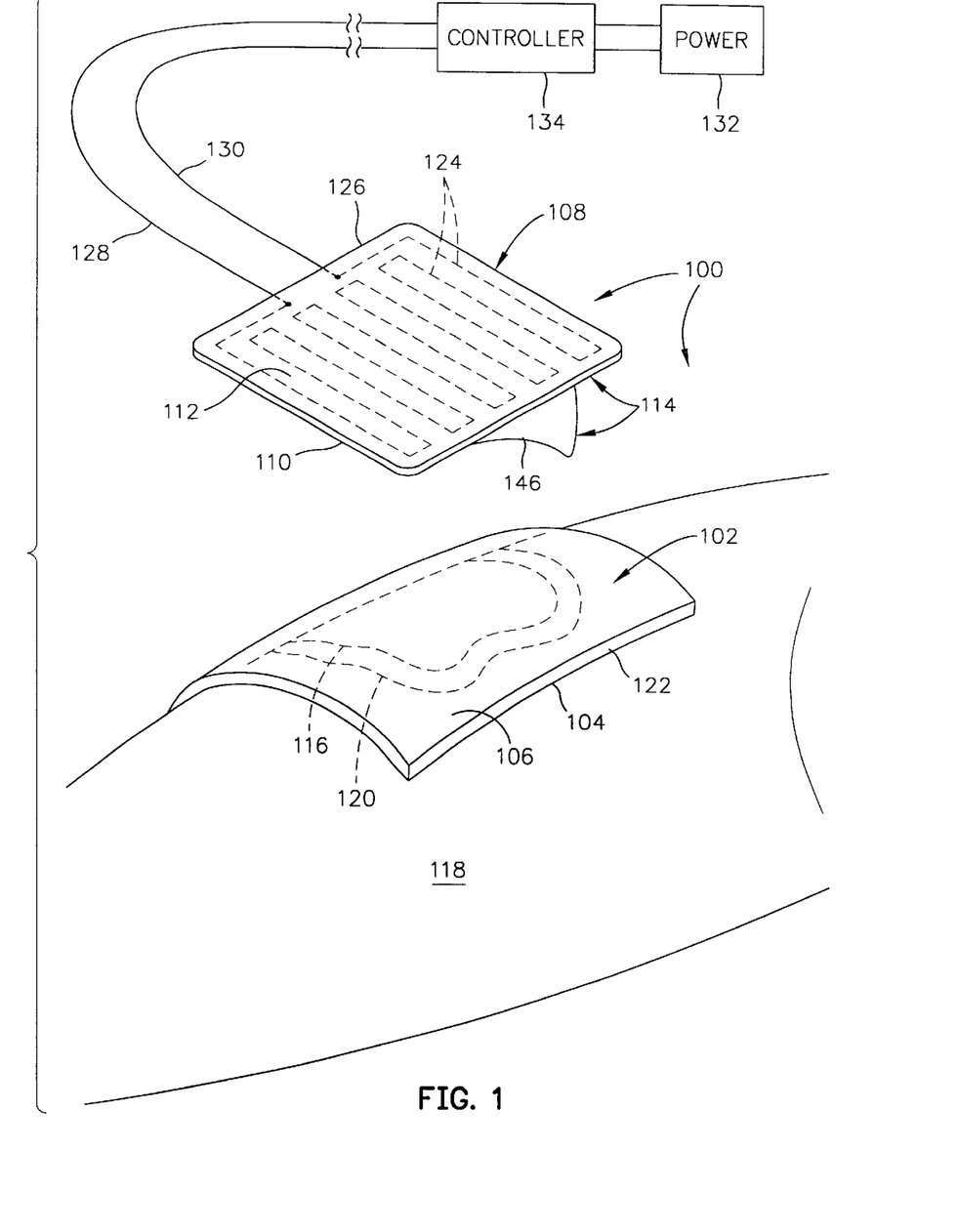
FIG. 1 is an isometric view of a first embodiment of the wound treatment apparatus being applied to a wound on a person's body.
Figure 2:
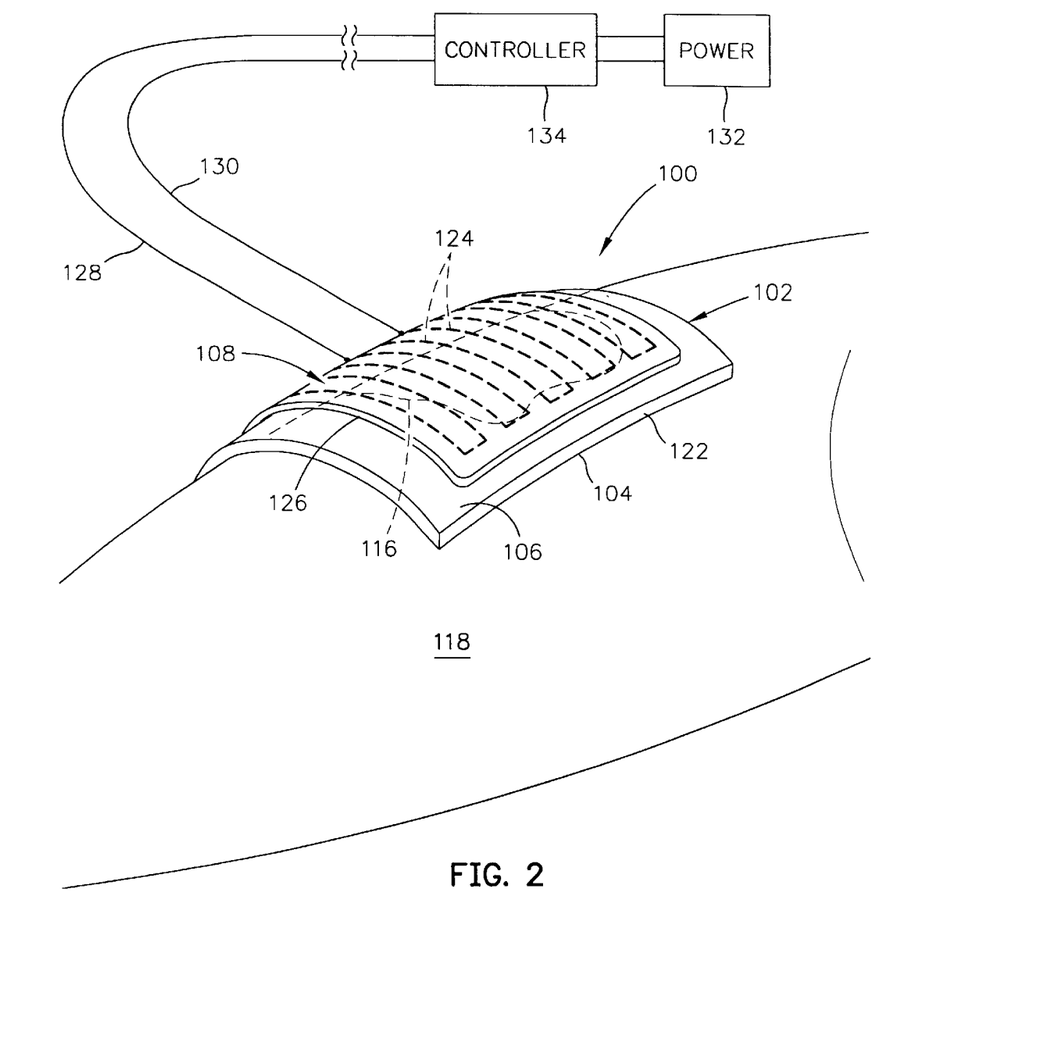
FIG. 2 is an isometric view of the wound treatment apparatus applied to the wound on the person's body.
Figure 3:
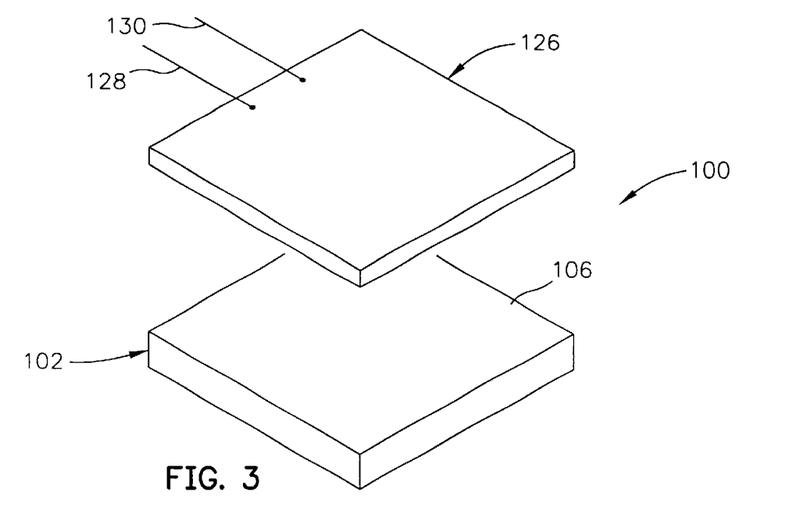
FIG. 3 is an exploded isometric view of the wound treatment apparatus.
Figure 4:
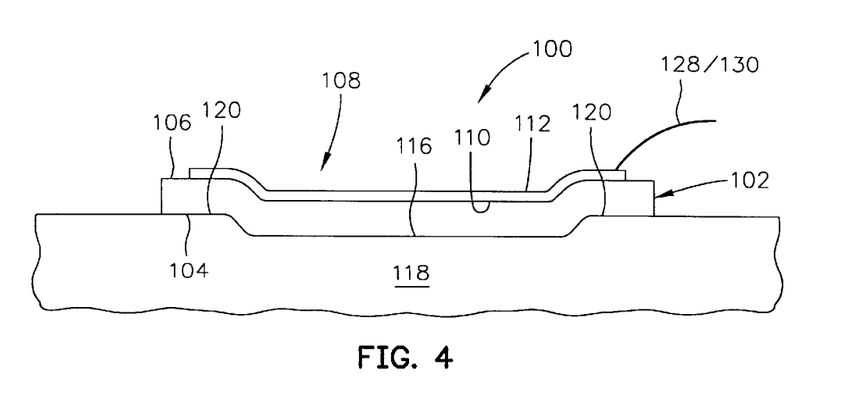
FIG. 4 is a cross-sectional view of the wound treatment apparatus applied to the wound on the person's body.

As shown in FIGS. 1–5, the wound treatment apparatus 100 includes a bandage 102 fabricated to absorb energy in the IR range. The bandage 102 has first (lower) and second (upper) surfaces 104 and 106. A heater 108 generates thermal energy and emits a significant amount of this energy in the IR range. The heater 108 includes first (lower) and second (upper) surfaces 110 and 112. An attachment means holds the heater 108 in position over the bandage 102 in such a manner as to transfer heat from the heater 108 through the bandage 102. The attachment means may maintain the second surface 106 of the bandage 102 and the first surface 110 of the heater 108 in full or partial contact or out of contact. In FIGS. 2 and 4, the wound treatment apparatus 100 is shown in place covering a wound 116 of a person's body 118. Immediately adjacent the wound is a periwound area 120 which is typically a peripheral band of tissue around the wound area with less trauma than the tissue of the wound area. The wound treatment apparatus 100 is capable of treating a wound treatment area that includes the wound and/or the periwound area, as desired.

In the wound treatment apparatus 100, the heater 108 includes means for generating heat that may be electrically operated. For example, the means may take the form of an electrical resistance element 124 embedded in or laminated to a planar member of flexible material 126, such as polyethylene, silicon, rubber or flexible cloth. In this regard, the heater 108 would form a "black body" that radiates heat in the form of energy in the IR range. In the preferred embodiment, the heater 108 is substantially planar, as shown in FIGS. 1 and 3, and yet flexible in order that it might conform, with the bandage 102, to the wound 116, as shown in FIG. 4, and to the person's body, as shown in FIGS. 2 and 4.

As illustrated in FIGS. 1 and 2, the electrical resistance element 124 is connected to first and second electrical conductors 128 and 130, which are connected to an electrical power source 132, via a controller 134. The purpose of the controller 134 is to control electrical power provided to the electrical resistance element 124. In this regard, the operation of the heater 108 may be cycled by the controller to maintain the tissue in the wound treatment area at a normothermic or a near normothermic temperature. As shown in FIGS. 1 and 2, the electrical resistance element 124 may extend back and forth in the flexible planar member 126 with a desired spacing to promote uniform heating of the heater 108.

Figure 5:
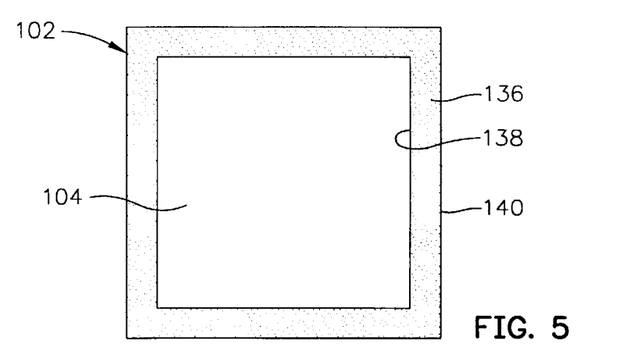
FIG. 5 is a plan view of a second surface of a wound treatment apparatus bandage.

As shown in FIG. 5, the first surface 104 of the bandage 102 is provided with a pattern of adhesive 136 adjacent its periphery. The adhesive pattern 136 may completely encompass the wound and the periwound areas so as to trap the natural moisture of the body which, in turn, maintains a moist environment across the wound treatment area for wound therapy purposes. Accordingly, the pattern of adhesive 136 has inner and outer boundaries 138 and 140 wherein, in the preferred embodiment, the outer boundary 140 coincides with the outer perimeter of the bandage 102. It should be understood that the bandage 102, the heater 108, and the pattern of adhesive 136 may take various shapes, such as the square shown in the drawings, or a rectangle, circle or ellipse, or any other regular or irregular shape, depending upon various shapes of wound treatment areas.

The bandage 102 is a flexible, planar member that is fabricated from a material or with a structure (or both) that absorbs energy in the IR range. The bandage 102 may be made using materials and structures that fall generally into two categories: 1.) water-containing materials; and, 2.) opaque, or painted, materials.

Water is highly absorptive of IR energy. Some of the water containing materials that may be used to fabricate the bandage 102 include: hydrogels, hydrocolloids, hydrated gauze, hydrated foam materials and hydrated alginates. An optional thin layer of IR-translucent polymeric film may be applied to the second surface 106 of the bandage 102 when the bandage is made from any of these materials. The thin layer of film will contain the moisture within the bandage 102 and protect the bandage 102 from the environment.

Alternately, the bandage 102 may be fabricated with films of certain polymeric materials. Any of these films may be used as an IR-absorbent layer which may or may not be used in combination with a hydrated layer that comprises the water-containing materials set forth above. Polymeric films absorb IR-energy depending on: 1.) the thickness of the film (greater that 5 mil thick is more absorptive than thinner films), 2.) opacity (opaque is more absorptive than transparent), 3.) a color applied to at least one surface of film (a colored surface of flat white or flat black is preferred). An IR film that includes one or more of these characteristics is preferable.

Since human body tissue comprises a large amount of water, the IR energy generated by the heater 108 and absorbed by the bandage 102 will be absorbed by the tissue in and near the wound treatment area, thereby warming the tissue. Manifestly, the structure of the wound treatment apparatus 100 as thus far described maintains a closed, moist, heated environment at and over the wound treatment area to promote fast healing of wounded tissue.

Figure 6A:
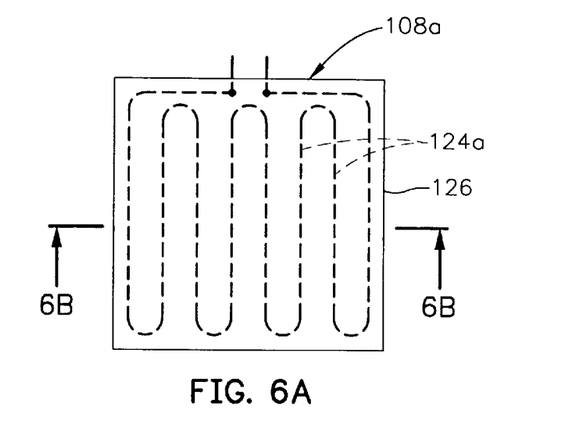
FIG. 6A is a planar illustration of an electrical resistance element embedded in a flexible layer for uniform heating.
Figure 6B:
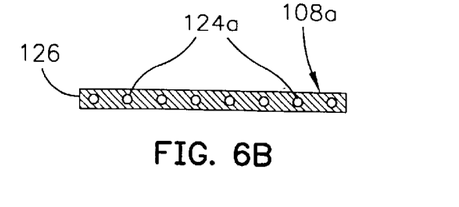
FIG. 6B is a view taken along plane VIB of VIB FIG. 6A.
Figure 7A:
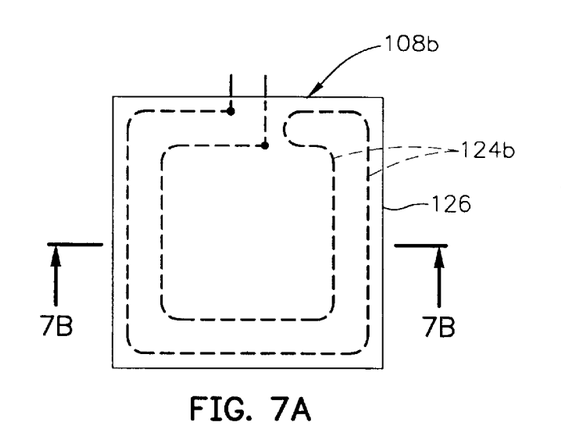
FIG. 7A is a planar view of an electrical resistance element embedded in a flexible layer for heating a portion of a treatment area.
Figure 7B:
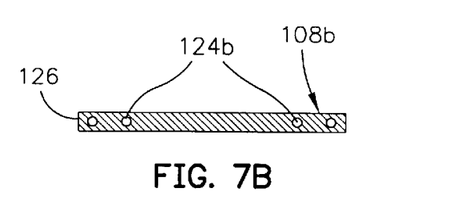
FIG. 7B is a view taken along plane VIIB—VIIB of FIG. 7A.
Figure 8A:
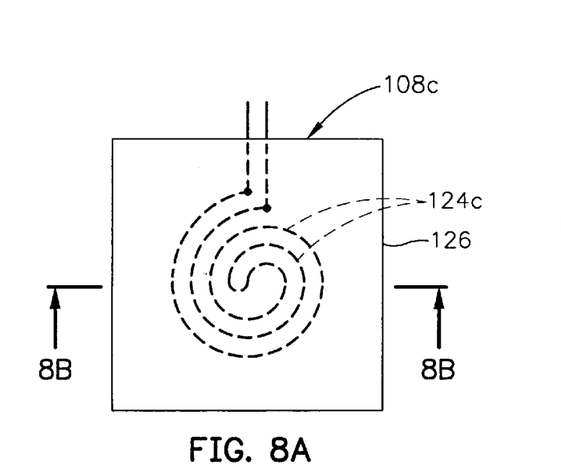
FIG. 8A is a planar view of an electrical resistance element embedded in a flexible layer for uniform heating of a central portion of a treatment area.
Figure 8B:
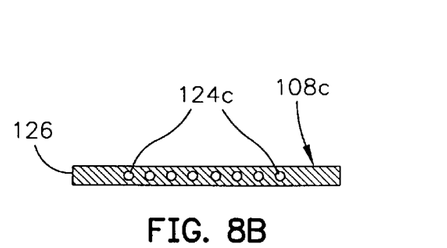
FIG. 8B is a view taken along plane VIIIB—VIIIB of FIG. 8A.

FIGS. 6–8 illustrate various embodiments of electrical resistance elements for the heater 108. In the heater 108a shown in FIG. 6A, an electrical resistance element 124a winds back and forth within the flexible planar member 126, similar to what is shown in FIG. 1. The spacing between the windings of the electrical resistance element 124a may be sized so as to ensure substantially uniform heating of the heater 108a. FIG. 6B shows the electrical resistance element embedded or laminated in the flexible planar member 126. In FIG. 7A, the electrical resistance element 124b takes a path along a peripheral zone of the flexible planar member 126, so that the periphery of the heater 108b is uniformly heated to a temperature greater than a central portion of the heater. Again, these electrical resistance elements 124b are shown embedded or laminated in the flexible planar member 126 in FIG. 7B. In FIG. 8A, the electrical resistance element 124c takes a spiral path out and back within a central region of the heater 108c so as to uniformly heat the central region of the heater to a higher temperature than regions outbound therefrom. The heater 108a is adapted for applying heat to both the wound and periwound area 116 and 120 in FIG. 4, the heater 108b is adapted for applying heat primarily to the periwound area 120 and the heater 108c is adapted for applying heat primarily to the wound 116.

Although the means in the heater 108 for generating heat is disclosed and described above as being electrically-actuated, this is not intended to limit the heater 108 solely to electrical operation. In fact, other heat generating means that would be suitable for the heater 108 include, without limitation, chemical heaters, water pad heaters, and phase-change salt heaters. Chemical heaters and phase-change salt heaters would preferably be formed into a relatively thin pad and sealed in a pouch made of polymeric film. A water pad heater can be fabricated by thermo-forming two sheets of polymeric film into fluid channels and sealing the sheets at their peripheries. Warm water is then circulated through the pad from an external source of hot water.

Many surfaces of the body have convexities and concavities in close proximity to one another. See for example the profile of the person's body 118 in the vicinity of the wound 116 in FIG. 4. The ability of the bandage 102 to absorb energy in the IR region, is important because of the difficulty in achieving a continuous, uniform thermal contact for conductive heat transfer between the second surface 106 of the bandage 102 and the first surface 110 of the heater 108, even when the heater 108 is fabricated to be moderately flexible and substantially planar. Even a highly flexible planar heater will tend to rest on top of the convexities and not touch the bottom of the concavities. For example, consider the profile of an ulcer on the skin. Consider further that base of the ulcer is sharply recessed. In this case, the base of the ulcer may not even be contacted by the first surface 104 of the bandage 102.

Figure 9A:
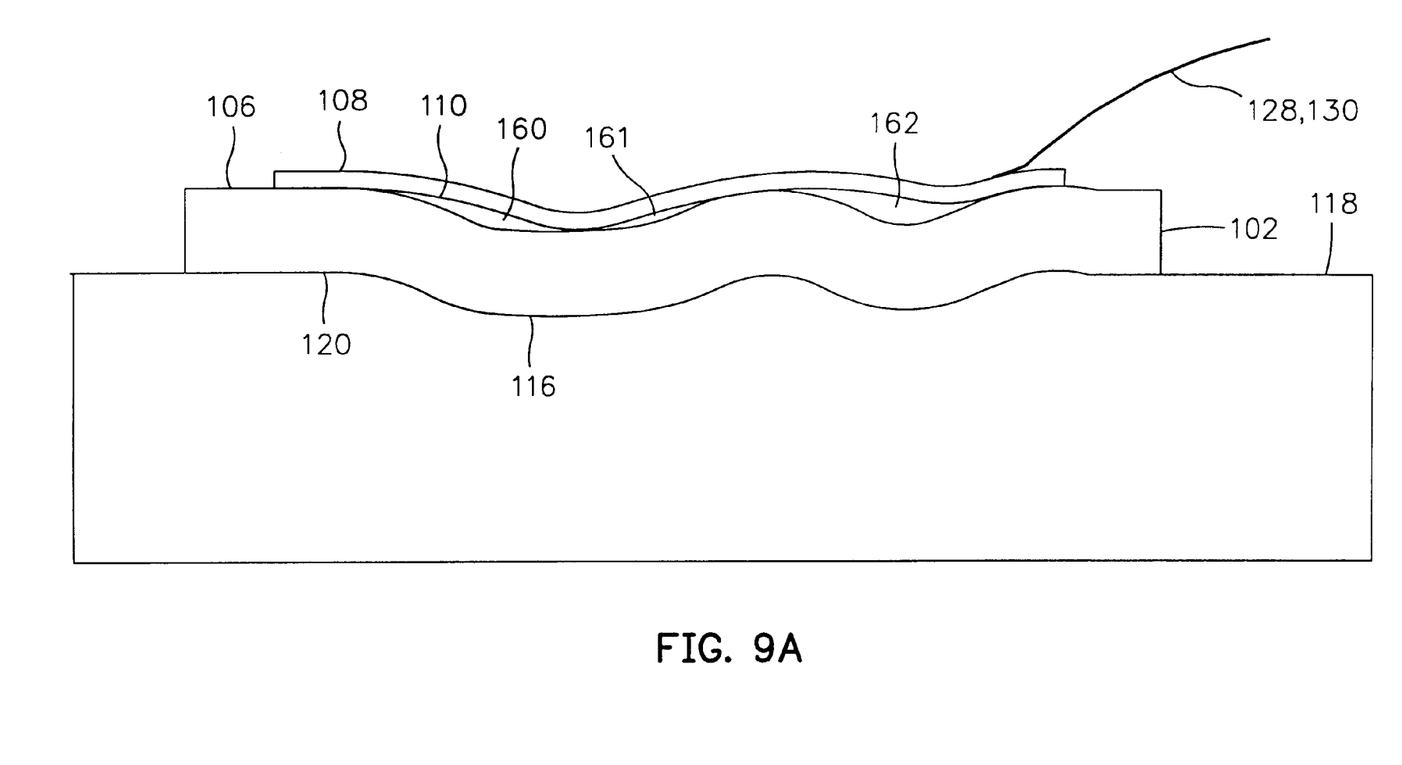
FIG. 9A is a side sectional view of the wound treatment apparatus applied to a wound, with areas of non contact between heater and bandage.

The invention contemplates that the first surface 110 of the heater 108 may be in full, or partial contact with the second surface 106 of the bandage 102. For example, in FIG. 9A, there is less than full contact between the surfaces 110 and 106. In the areas where the first surface 110 and the second surface 106 are in contact, heat will be transferred by conduction between the first surface 110 and the second surface 106. However, it may be very difficult to conform even the most flexible, substantially planar configuration of the heater 108 to the contours of the human body, and further to the contours of any particular wound such as the wound 116. Therefore, in many cases, areas of non-contact between the heater 108 and the second surface 106 will exist, creating air spaces 160, 161, and 162 which act as pockets of thermal insulation.

Figure 9B:
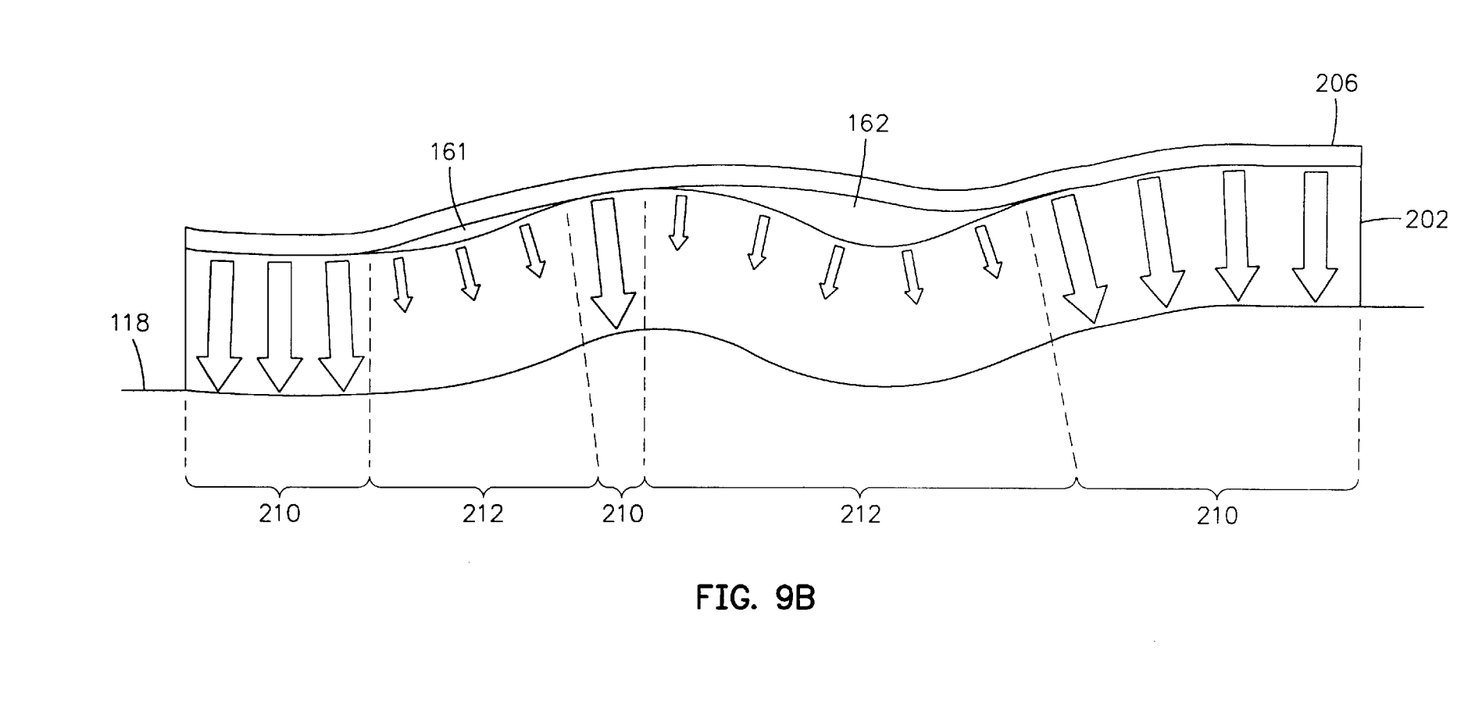
FIGS. 9B and 9C are magnified view of a detail in FIG. 9A enclosed in a circle.

In prior art heater/bandage combinations such as that shown in FIG. 9B only inefficient convective heat transfer occurs in air spaces 161 and 162 because the bandage 202 is not transparent in the IR region. The regions of contact (supporting conductive heat transfer) 210 and the regions of non-contact (supporting convective heat transfer) 212 may have large and unpredictable differences in temperature and heat transfer, resulting in substantial non-uniformities in distribution of the heat across the prior art bandages 202. The result is that, with prior art heater/bandage combinations, heating of the wound treatment area may be uneven, and ineffective in treating a wound.

Figure 9C:
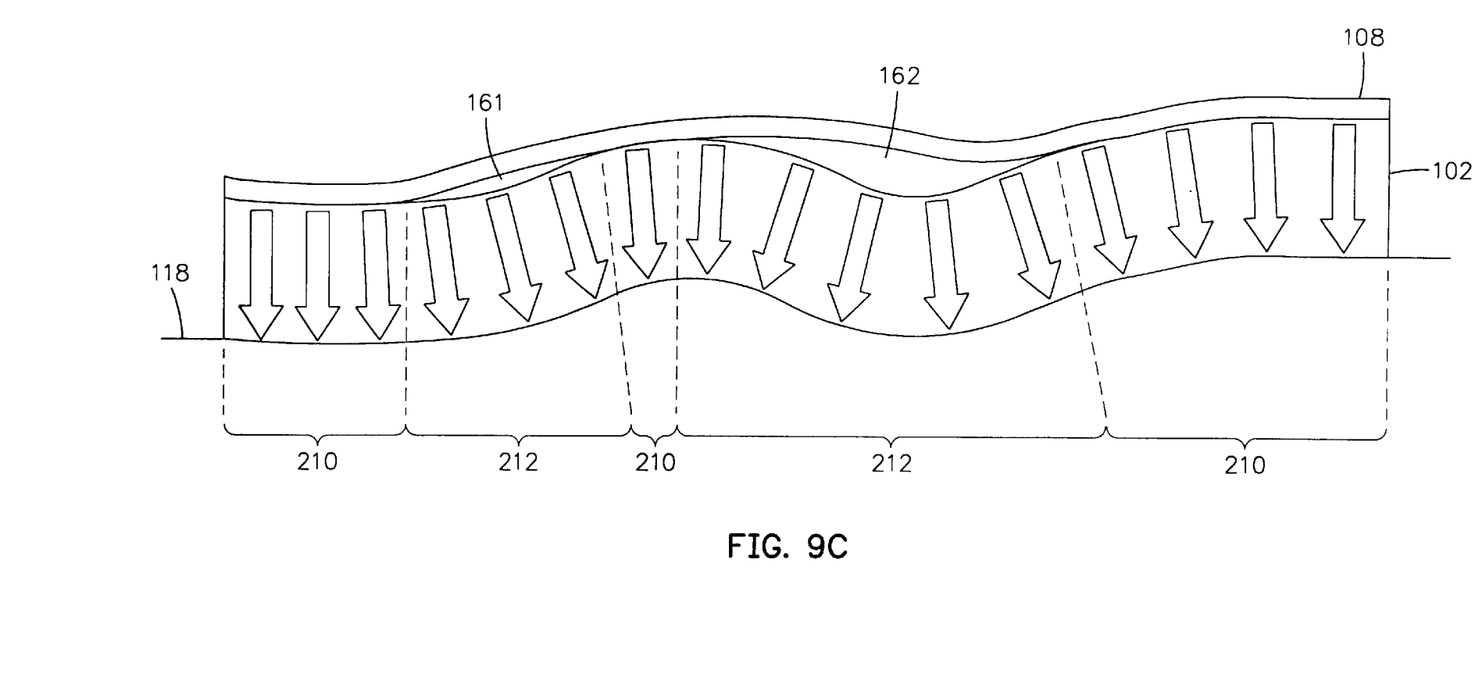

As FIG. 9C shows, with the bandage 102 being fabricated so as to absorb energy in the IR range, and with the heater 108 acting as a radiating black body, a significant component of heat is transferred to the bandage 102 by radiation. Therefore, in the regions 212 where the first surface 110 of the heater 108 does not contact the second surface 106 of the bandage 102, significant amounts of heat will be transferred by radiation. The invention therefore overcomes the inherent unevenness of heat transfer to the wound treatment area in the prior art heater/bandage lead combinations where heat transfer from heater to bandage is by conduction and convection only. In this invention, heat transfer between the heater 108 and the bandage 102 is by conduction, convection, and radiation. This provides more efficient, and more uniform, heat transfer from the heater 108 to the bandage 102. This creates a more uniform distribution of heat in, and across, the bandage 102, providing a more even and predictable distribution of heat across the tissue in and near the wound treatment area.

This invention further improves on the prior art modes of heating a wound with IR energy as, for example, where wounds are exposed to the output of high temperature heat lamps. In these case, the heat lamps shine on open, exposed wound treatment areas, causing drying of wound tissue, which inhibits and delays healing. This invention interposes an IR absorptive bandage layer between the IR heat source and the wound which seals about the wound, retaining moisture at the wound and preventing its drying.

The third component of this invention is an attachment means to hold the heater 108 in position on, or over, the bandage 102. Such means may include, for example, a pattern of adhesive that acts between the first surface 110 of the heater 108 and the second surface 106 of the bandage 102. The pattern may have, for example, the shape and composition of the pattern illustrated in FIG. 5. This pattern of adhesive may be on the second surface 106 of the bandage 102 or on the first surface 110 film of two of the heater 108. Alternatively, it may comprise a separate film of two sided adhesive between the surfaces 106 and 110. Other attachment means contemplated for use in this invention include, without limitation, hook-and-eye material, a pocket formed on the first surface 106 of the bandage 102, tabs, tapes, straps, clamps, and so forth. The function of the attachment means is to hold the heater 108 in close proximity to the bandage 102. The function may result in full or partial contact between the first surface 110 of the heater 108 and the second surface 106 of the bandage 102, or may even result in the heater 108 being held slightly off of the second surface 106, out of direct contact with the bandage 102.

Clearly, other embodiments and modifications of this invention will occur readily to those of ordinary skill in the art in view of these teachings. Therefore, this invention is to be limited only by the following claims, which include all such embodiments and modifications when viewed in conjunction with the above specification and accompanying drawings.

What is claimed is:

1. A wound treatment apparatus comprising:
a bandage having first and second surfaces, the first surface of the bandage defining a wound treatment area corresponding to a wound site on a person;
the bandage being absorptive of energy in the infrared (IR) range of the electromagnetic spectrum;
a heater;
the heater being positioned over the second surface of the bandage substantially over the wound treatment area; and
an attachment means acting between the heater and the second surface for retaining the heater over the bandage's second surface.

2. A treatment apparatus comprising:
a bandage having first and second surfaces;
the bandage being absorptive of infrared (IR) energy;
a heater positioned over the second surface of the bandage; and
adhesive acting between the heater and the second surface of the bandage.

3. The treatment apparatus of claim 2, further including an adhesive pattern on the first surface of the bandage.

4. The treatment apparatus of claim 2, further including means for adhering the first surface of the bandage to a person's skin.

5. The treatment apparatus of claim 4, wherein the means include a pattern of adhesive material on the first surface of the bandage.

6. The treatment apparatus of claim 2, the bandage being a flexible, planar member fabricated of a material selected from the group including hydrogels, hydrocolloids, hydrated gauze, hydrated foam, and hydrated alginates.

7. The treatment apparatus of claim 2, the bandage being a polymeric film.

8. The treatment apparatus of claim 7, wherein the polymeric film has a thickness of 5 mils.

9. The treatment apparatus of claim 7, wherein the polymeric film has a thickness of greater than 5 mils.

10. The treatment apparatus of claim 7, wherein the polymeric film is opaque.

11. The treatment apparatus of claim 7, wherein at least one surface of the polymeric film is colored.

12. The treatment apparatus of claim 2, wherein the heater is planar.

13. The treatment apparatus of claim 2, wherein the heater is flexible.

14. The treatment apparatus of claim 2, including means for uniformly heating the heater.

15. The treatment apparatus of claim 2, including means for heating a portion of the heater.

16. The treatment apparatus of claim 2, wherein the heater has a first surface and the adhesive acts between the first surface of the heater and the second surface of the bandage.

17. The treatment apparatus of claim 16, wherein a portion of the first surface of the heater contacts a portion of the second surface of the bandage.

18. The treatment apparatus of claim 16, wherein the first surface of the heater partially contacts the second surface of the bandage.

19. The treatment apparatus of claim 16, wherein the adhesive includes a pattern of adhesive acting between the first surface of the heater and the second surface of the bandage.

20. The treatment apparatus of claim 2, wherein the adhesive includes a pattern of adhesive between the heater and the second surface of the bandage.

21. The treatment apparatus of claim 2 wherein the heater is electrically actuated.

22. The treatment apparatus of claim 20, wherein the heater includes a flexible planar member and an electrical resistance element in the flexible planar member.

* * * * *